United States Patent [19]

Hilboll et al.

[11] Patent Number: 4,667,033

[45] Date of Patent: * May 19, 1987

[54] SUBSTITUTED 6-(THIEN-2-YL)-3(2H)-PYRIDAZINONES

[75] Inventors: Gerd Hilboll, Cologne; Sigurd Leyck; Gerrit Prop, both of Pulheim, all of Fed. Rep. of Germany

[73] Assignee: A. Nattermann & Cie GmbH, Cologne, Fed. Rep. of Germany

[*] Notice: The portion of the term of this patent subsequent to Feb. 17, 2004 has been disclaimed.

[21] Appl. No.: 618,582

[22] Filed: Jun. 8, 1984

[30] Foreign Application Priority Data

Jun. 10, 1983 [DE] Fed. Rep. of Germany ....... 3321012

[51] Int. Cl.$^4$ ................. C07D 409/14; C07D 409/06; C07D 409/04; A61K 31/50

[52] U.S. Cl. ..................................... 544/114; 544/238; 548/255; 548/262; 548/300; 548/336; 548/348; 548/356; 548/374; 548/379; 548/517

[58] Field of Search ............................... 544/238, 114

[56] References Cited

U.S. PATENT DOCUMENTS

| | | | |
|---|---|---|---|
| 3,441,565 | 4/1969 | Laborit | 260/247.2 |
| 4,289,774 | 9/1981 | Schacht | 544/238 |
| 4,504,479 | 3/1985 | Lautenschlager | 544/238 |
| 4,507,298 | 3/1985 | Lautenschlager | 544/238 |
| 4,508,721 | 4/1985 | Hargreaves | 544/238 |
| 4,521,416 | 6/1985 | Sircar | 544/238 |

FOREIGN PATENT DOCUMENTS 75436  3/1983  European Pat. Off. ............ 544/238

OTHER PUBLICATIONS

Austel, Chem. Abs. 93, 114525(a) 1980.
Lautenschlaeger III, Chem. Abs. 98, 198225 (2-17-83).
Hilboll, Chem. Abs. 101, 72744x (1984).
Albright et al., Journal of Medicinal Chemistry, 1981, vol. 24, pp. 592–600.
Wiley et al., J. Org. Chem. 1953, 18, pp. 1368-1371.
Sitkina et al., Chemical Abstracts, 1966, vol. 65, 13686e.
Khan et al., J. Chem. Soc. C., 1970, p. 85 ff.
S. Granowitz and S. Liljefors, Chemica Scripta 13, 1979, pp. 157-161.
H. Stetter, Angewandte Chemie, vol. 15, No. 11, 1976.
Steck et al., J. Heterocycl. Chem., 11, 1974, p. 755 ff.
Ismail et al., Indian J. Chem., 21B, 1982, p. 371.
Steiner, Journal of Medicinal Chemistry, 1981, vol. 24, pp. 59-61.
Sederic, Chemical Abstracts, 1967, vol. 66, 28791v.
Damm et al., Research Communications in Chemical Pathology and Pharmacology, vol. 22, No. 3, 1978.
M. Briley et al., European Journal of Pharmacology, 72, 1981, pp. 377-380.

Primary Examiner—Mark L. Berch
Attorney, Agent, or Firm—Pearne, Gordon, McCoy & Granger

[57] ABSTRACT

The invention refers to substituted 6-(thien-2-yl)-3(2H)-pyridazinones of Formula I

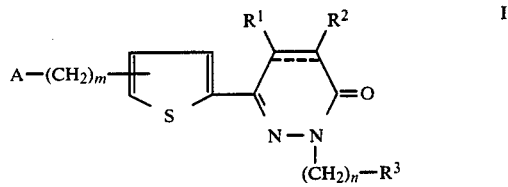

2 Claims, No Drawings

SUBSTITUTED 6-(THIEN-2-YL)-3(2H)-PYRIDAZINONES

The present invention refers to substituted 6-(thien-2-yl)-3(2H)-pyridazinones of formula I

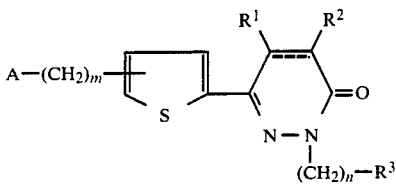

wherein
A is a saturated, partly saturated or heteroaromatic five-membered ring system (i.e. heterocyclus) containing 1 to 3 nitrogen atoms, the ring system being bonded to the neighbouring carbon atom through one of its nitrogen atoms and being unsubstituted or substituted by 1 or 2 $C_{1-4}$-lower alkyl radicals,
m is zero or an integer from 1 to 5,

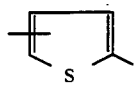

is 2.5- or 2.4-substituted thienyl, i.e. the group A—$(CH_2)_m$— is bonded to the thienyl ring in its 5- or 4-position,
$R^1$ and $R^2$ which may be the same or different from each other, are hydrogen or methyl,
n is zero or an integer from 2 to 4,
$R^3$ is hydrogen, if n is zero, or is di-$C_{1-4}$-lower alkylamino, morpholino, pyrrolidino or piperidino, if n is not zero, and
═══ is a single bond between two carbon atoms, if n is zero, or is a double bond between two carbon atoms, if n is not zero,
except the compounds wherein both A is unsubstituted imidazole and ═══ is a single bond.

A group of preferred 6-(thien-2-yl)-3(2H)-pyridazinone compounds are those of formula I wherein
A is a saturated, partly saturated or heteroaromatic five-membered heterocyclus containing 1 to 3 nitrogen atoms, bondet to the neighbouring carbon atom through one of its nitrogen atoms and being unsubstituted or substituted by 1 or 2 $C_{1-4}$-lower alkyl group, such as pyrrolidine, pyrrole, pyrazole, triazole, 2-methylimidazole, 4.5-diethylimidazole, except the unsubstituted imidazole,
m is zero or 1,
$R^1$ and $R^2$ which may be the same or different from each other, are hydrogen or methyl,
n is zero,
$R^3$ is hydrogen and
═══ is a single bond
and the group A—$(CH_2)_m$— being in the 4- or 5-position of the thienyl ring.

Another group of preferred 6-(thien-2-yl)-3(2H)-pyridazinone compounds are those of formula I, wherein
A is a saturated, partly saturated or heteroaromatic five-membered heterocyclus containing 1 to 3 nitrogen atoms, bonded to the neighbouring carbon atom through one of its nitrogen atoms and being unsubstituted or substituted by 1 or 2 $C_{1-4}$-lower alkyl groups such as pyrrolidine, pyrrole, pyrazole, imidazole, 2-methylimidazole, triazole, or 4.5-diethylimidazole,
m is zero or an integer from 1 to 5,
$R^1$ and $R^2$ which may be the same or different from each other, are hydrogen or methyl,
n is zero, 2, 3 or 4, i.e is zero or an integer from 2 to 4,
$R^3$ is hydrogen, if n is zero, or is di-$C_{1-4}$-lower alkylamino, morpholino, pyrrolidino or piperidino, if n is not zero, and
═══ is a double bond,
and the group A—$(CH_2)_m$— being in the 4- or 5-position of the thienyl ring.

Included are also the pharmaceutically acceptable salts of compounds of formula I with inorganic or organic salts such as the hydrochlorides, acetates, fumarates, citrates or benzoates.

The compounds of formula I wherein n is 0 and $R^3$ is hydrogen are present in equilibrium with the corresponding tautomeric 4.5-dihydro-6-(thien-2-yl)-3(2H)-3-hydroxypyridazines (i.e. ═══ is a single bond) and 6-(thien-2-yl)-3(2H)-3-hydroxy-pyridazines (i.e. ═══ is a double bond), respectively.

The 4.5-dihydro-6-(thien-2-yl)-3(2H)-pyridazinones of formula I have a chirality center at positions 4 and 5, respectively, of the pyridazine ring if the substituents $R^1$ and/or $R^2$ are different from hydrogen and, thus, they can exist in form of their racemates or their enantiomers. If a separation of the racemates is desired, it is conveniently carried out by using processes known per se with optically active acids like dibenzoyl tartaric acid or camphor-10-sulfonic acid through the formation of diastereomeric salts, or by chromatography using an optically active column material.

The compounds of formula I have valuable pharmaceutical properties. A part of the compounds, in particular those of formula I wherein n is zero and, at the same time, $R^3$ is hydrogen, produce a positive inotropic effect with simultaneously little influence to blood pressure and heart pulse frequency. They therefore are useful as cardiotonics. Another group of the compounds, in particular those of formula I wherein n is not zero and, at the same time, $R^3$ is different from hydrogen, show a strong effectiveness upon the central nervous system. They therefore are useful for instance as tranquillizers, anticonvulsives or antidepressives.

Examples for the compounds of the invention are:
4,5-Dihydro-6-[5-(pyrrolidin-1-yl-methyl)-thien-2-yl]-3(2H)-pyridazinone;
4,5-Dihydro-6-[5-[2-(pyrrolidin-1-yl)-ethyl]-thien-2-yl]-3(2H)-pyridazinone;
4,5-Dihydro-6-[5-[3-(pyrrolidin-1-yl)-propyl]-thien-2-yl]-3(2H)-pyridazinone;
4,5-Dihydro-6-[5-[4-(pyrrolidin-1-yl)-butyl]-thien-2-yl]-3(2H)-pyridazinone;
4,5-Dihydro-6-[5-[5-pyrrolidin-1-yl)-pentyl]-thien-2-yl]-3(2H)-pyridazinone;
4,5-Dihydro-6-[5-(pyrrol-1-yl-methyl)-thien-2-yl]-3(2H)-pyridazinone;
4,5-Dihydro-6-[5-(pyrazol-1-yl)-thien-2-yl]-3(2H)-pyridazinone;
4,5-Dihydro-6-[4-pyrazol-1-yl-methyl)-thien-2-yl]-3(2H)-pyridazinone;
4,5-Dihydro-6-[5-(1,2,4-triazol-1-yl)-thien-2-yl]-3(2H)-pyridazinone;

4,5-Dihydro-5-methyl-6-[5-(1,2,4-triazol-1-yl)-thien-2-yl]-3(2H)-pyridazinone;
4,5-Dihydro-6-[5-(1,2,4-triazol-4-yl-methyl)-thien-2-yl]-3(2H)-pyridazinone;
6-[5-Pyrrolidin-1-yl-methyl)-thien-2-yl]-3(2H)-pyridazinone;
6-[5[2-(Pyrrolidin-1-yl)-ethyl]-thien-2-yl]-3(2H)-pyridazinone;
6-[5-[3-(Pyrrolidin-1-yl)-propyl]-thien-2-yl]-3(2H)-pyridazinone;
6-[5-[4-(Pyrrolidin-1-yl)-butyl]-thien-2-yl]-3(2H)-pyridazinone;
6-[5-[5-(Pyrrolidin-1-yl)-pentyl]-thien-2-yl]-3(2H)-pyridazinone;
6-[5-(Pyrrol-1-yl-methyl)-thien-2-yl]-3(2H)-pyridazinone;
6-[5-(Pyrazol-1-yl-methyl)-thien-2-yl]-3(2H)-pyridazinone;
6-[4-(Pyrazol-1-yl-methyl)-thien-2-yl]-3(2H)-pyridazinone;
6-[5-(Pyrazol-1-yl)-thien-2-yl]-3(2H)-pyridazinone;
4-Methyl-6-[5-(pyrazol-1-yl)-thien-2-yl]-3(2H)-pyridazinone;
5-Methyl-6-[5-(pyrazol-1-yl)-thien-2-yl]-3(2H)-pyridazinone;
6-[5-(Imidazol-1-yl)-thien-2-yl]-3(2H)-pyridazinone;
6-[5-(Imidazol-1-yl)-thien-2-yl]-4-methyl-3(2H)-pyridazinone;
6-[5-(Imidazol-1-yl)-thien-2-yl]-5-methyl-3(2H)-pyridazinone;
6-[5-(Imidazol-1-yl-methyl)-thien-2-yl]-3(2H)-pyridazinone;
6-[5-[2-(Imidazol-1-yl)-ethyl]-thien-2-yl]-3(2H)-pyridazinone;
6-[4-(Imidazol-1-yl)-thien-2-yl]-3(2H)-pyridazinone;
6-[4-(Imidazol-1-yl)-thien-2-yl]-4-methyl-3(2H)-pyridazinone;
6-[4-(Imidazol-1-yl)-thien-2-yl]-5-methyl-3(2H)-pyridazinone;
6-[4-(Imidazol-1-yl-methyl)-thien-2-yl]-3(2H)-pyridazinone;
6-[5-[3-(Imidazol-1-yl)-propyl]-thien-2-yl]-3(2H)-pyridazinone;
6-[5-[4-(Imidazol-1-yl)-butyl]-thien-2-yl]-3(2H)-pyridazinone;
6-[5-[5-(Imidazol-1-yl)-pentyl]-thien-2-yl]-3(2H)-pyridazinone;
6-[5-(2-Methyl-imidazol-1-yl-methyl)-thien-2-yl]-3(2H)-pyridazinone;
6-[4-(2-Methyl-imidazol-1-yl-methyl)-thien-2-yl]-3(2H)-pyridazinone;
6-[5-(4,5-Diethyl-imidazol-1-yl)-thien-2-yl]-3(2H)-pyridazinone;
6-[5-(1,2,4-Triazol-1-yl)-thien-2-yl]-3(2H)-pyridazinone;
5-Methyl-6-[5-(1,2,4-triazol-1-yl)-thien-2-yl]-3(2H)-pyridazinone;
6-[5-(1,2,4-Triazol-4-yl)-thien-2-yl]-3(2H)-pyridazinone;
2-(2-Diethylaminoethyl)-5-methyl-6-[5-(imidazol-1-yl)-thien-2-yl]-3(2H)-pyridazinone;
6-[5-(Imidazol-1-yl)-thien-2-yl]-2-(2-morpholino-ethyl)-3(2H)-pyridazinone.
2-(2-Morpholino-ethyl)-6-[5-(pyrazol-1-yl-methyl)-thien-2-yl]-3(2H)-pyridazinone;
5-Methyl-2-[2-(pyrrolidin-1-yl)-ethyl]-6-[5-(pyrazol-1-yl)-thien-2-yl]-3(2H)-pyridazinone;
6-[5-(Imidazol-1-yl)-thien-2-yl]-2-(2-piperidino-ethyl)-3(2H)-pyridazinone;
6-[4-(Imidazol-1-yl)-thien-2-yl]-2-(2-morpholino-ethyl)-3(2H)-pyridazinone;
6-[4-(Imidazol-1-yl)-thien-2-yl]-5-methyl-2-(2-diethylamino-ethyl)-3(2H)-pyridazinone;
2-(2-Morpholino-ethyl)-6-[5-(pyrrolidin-1-yl-methyl)-thien-2-yl]-3(2H)-pyridazinone;
6-[4-(Imidazol-1-yl)-thien-2-yl]-4-methyl-2-(2-morpholino-ethyl)-3(2H)-pyridazinone;
6-[5-(Imidazol-1-yl-methyl)-thien-2-yl]-2-(2-morpholino-ethyl)-3(2H)-pyridazinone;
6-[5-(Imidazol-1-yl-methyl)-thien-2-yl]-2-(2-piperidino-ethyl)-3(2H)-pyridazinone;
6-[5-(Imidazol-1-yl-methyl)-thien-2-yl]-2-(3-piperidino-propyl)-3(2H)-pyridazinone;
6-[5-(Imidazol-1-yl-methyl)-thien-2-yl]-2-(2-pyrrolidino-ethyl)-3(2H)-pyridazinone;
2-(2-Diethylamino-ethyl)-6-[5-(imidazol-1-yl-methyl)-thien-2-yl]-3(2H)-pyridazinone;
6-[5-(Imidazol-1-yl-methyl)-thien-2-yl]-2-(4-piperidino-butyl)-3(2H)-pyridazinone;
6-[4-(Imidazol-1-yl-methyl)-thien-2-yl]-2-(3-piperidino-propyl)-3(2H)-pyridazinone;
6-[4-(Imidazol-1-yl-methyl)-thien-2-yl]-2-(2-piperidino-ethyl)-3(2H)-pyridazinone;
6-[4-(Imidazol-1-yl-methyl)-thien-2-yl]-2-(2-morpholino-ethyl)-3(2H)-pyridazinone.

The preparation of the compounds of the invention is carried out using processes known per se. For example, the 6-(thien-2-yl)-3(2H)-pyridazinones of formula I wherein ≡≡≡ is a single bond, n is zero and $R^3$ is hydrogen, are prepared by reacting the 4-oxo-butyric acids of formula II or the alkylesters thereof, wherein A, m, $R^1$ and $R^2$ are defined as in formula I, with hydrazine, the hydrate or a salt thereof, such as the hydrochloride, hydrogensulfate, sulfate and the like, in water, water-lower alkanol-mixtures or in a lower alkanol as solvent, i.e. in aqueous, aqueous-alcoholic or alcoholic medium, or in another solvent inert under the selected conditions, such as dioxane, toluene, dimethylformamide or mixtures thereof with water and/or alcohol at a temperature of from 30° to 150° C., optionally by using a catalyst as commonly used in aminolysis and condensation reactions such as barium oxide, preferably at a temperature of from 80° to 100° C. in ethanol or water.

The reactions proceed as follows:

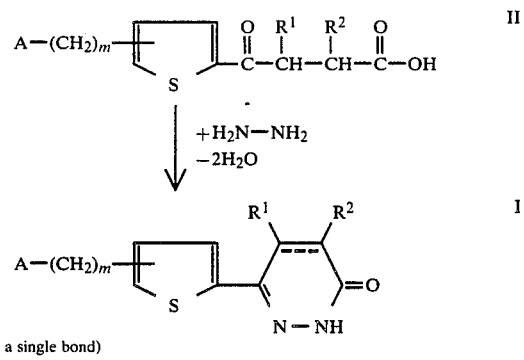

(≡≡≡ is a single bond)

Examples for starting compounds of formula II are in particular:

4-Oxo-4-[5-(pyrrolidin-1-yl-methyl)-thien-2-yl]-butyric acid;
4-Oxo-4-[5-[2-(pyrrolidin-1-yl)-ethyl]-thien-2-yl]-butyric acid;

4-Oxo-4-[5-[3-(pyrrolidin-1-yl)-propyl]-thien-2-yl]-butyric acid;
4-Oxo-4-[5-[4-(pyrrolidin-1-yl)-butyl]-thien-2-yl]-butyric acid;
4-Oxo-4-[5-[5-(pyrrolidin-1-yl)-pentyl]-thien-2-yl]-butyric acid;
4-Oxo-4-[4-(pyrrolidin-1-yl-methyl)-thien-2-yl]-butyric acid;
4-Oxo-4-[5-(pyrrol-1-yl-methyl)-thien-2-yl]-butyric acid;
4-Oxo-4-[5-(pyrazol-1-yl)-thien-2-yl]-butyric acid;
3-Methyl-4-oxo-4-[5-(pyrazol-1-yl)-thien-2-yl]-butyric acid;
2-Methyl-4-oxo-4-[5-(pyrazol-1-yl)-thien-2-yl]-butyric acid;
4-Oxo-4-[5-(pyrazol-1-yl-methyl)-thien-2-yl]-butyric acid;
4-Oxo-4-[4-(pyrazol-1-yl-methyl)-thien-2-yl]-butyric acid;
4-Oxo-4-[5-(1,2,4-triazol-1-yl)-thien-2-yl]-butyric acid;
3-Methyl-4-oxo-4-[5-(1,2,4-triazol-1-yl)-thien-2-yl]-butyric acid;
4-Oxo-4-[5-(1,2,4-triazol-4-yl-methyl)-thien-2-yl]-butyric acid.

The preparation of the 4-oxo-butyric acids of formula II is carried out by using processes known per se:

(a) Starting compounds of formula II wherein m is not zero: The alkylthiophenes terminally substituted at the alkyl radical by the heterocyclus through one of its nitrogen atoms and having the formula IV wherein A and m are defined as in formula I are prepared for example analoguously to known processes by alkylating the heterocyclus A-H with an ω-halogeno alkylthiophene, optionally in an inert organic solvent such as toluene or dimethylformamide, and optionally by using an auxiliary base, such as sodium hydride and by using specific processes, respectively. For instance 2-(pyrrol-1-yl-methyl)-thiophene is obtained by subjecting 2-aminomethyl-thiophene to reaction with 2.5-dimethoxytetrahydrofurane analoguously to J. Med. Chem. 1981, 24, pgs. 592–600; 2-(1.2.4-triazolo-4-yl-methyl)-thiophene is obtained by subjecting 2-aminomethylthiophene to reaction with N,N-diformylhydrazine analoguously to J. Org. Chem. 18 (1953), p. 1368.

The further reaction with succinic acid alkylester chloride is carried out analoguously to DE-OS No. 31 30 250 and DE-OS No. 31 30 254 in the presence of an inert organic solvent such as 1.2-dichloroethane, nitrobenzene or carbon disulfide and by using a Friedel-Crafts catalyst such as aluminum chloride. This reaction leads to the alkylesters of the 4-oxobutyric acids of formula II which can be hydrolized by using known processes to form the corresponding 4-oxobutyric acids.

The reactions proceed as follows:

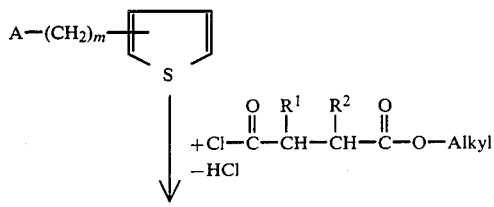

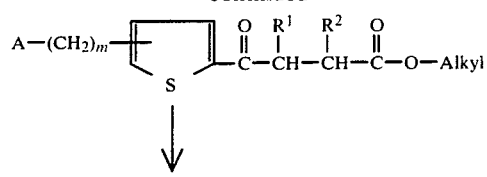

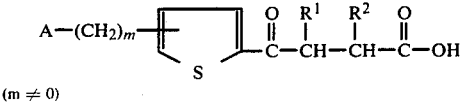

(m ≠ 0)

(b) Starting compounds of formula II wherein m is zero. Thiophen-2-aldehydes substituted by a heterocyclus through one of its nitrogen atoms having formula V wherein A is defined as in formula I and m is zero, are for example prepared by reacting the nitrogen heterocyclus A-H with 4- or 5-bromo-thiophen-2-aldehyde, prepared analoguously to C.A. 65 (1966), 13686e and J. Chem. Soc. C, 1970, p. 85 ff. and by using specific processes. For example 1-(5-formyl-thien-2-yl)-pyrazole, also analoguously to S. Gronowitz (Chem. Scr. 13 (1979), pgs. 157–161), is prepared by metallizing 1-(thien-2-yl)-pyrazole with butyllithium and subsequently reacting the resulting product with dimethylformamide using tetrahydrofurane as solvent.

The compounds of formula V are reacted with 2-alkenic acid nitriles using sodium cyanide as catalyst (see H. Stetter, Angew. Chem. 88 (1976), pgs. 695–736) to form the corresponding 4-oxo-butyric acid nitriles of formula VI which are converted to the corresponding 4-oxo-butyric acids by the acidic hydrolysis.

The reactions proceed as follows:

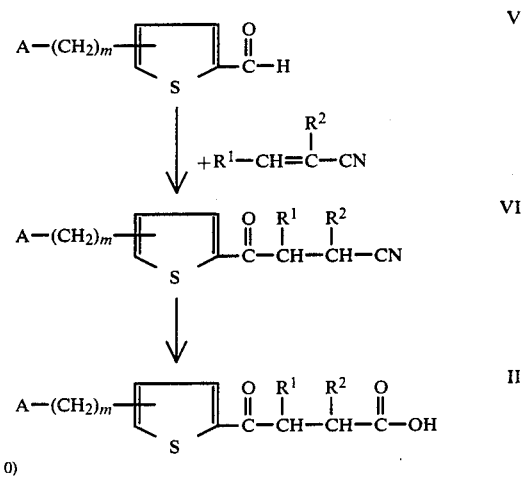

(m = 0)

The 3(2H)-pyridazinones of formula I where ≡≡≡ is a double bond, n is zero and R³ is hydrogen, are prepared by using processes known per se from a corresponding 4.5-dihydro-3(2H)-pyridazinone above mentioned or mentioned in EP No. 71059 by reacting it with a dehydrogenating agent such as bromine, selenium dioxide or the sodium salt of 3-nitro-benzene-sulfonic acid (see J. Heterocycl. Chem. 11 (1974), p. 755; Indian J. Chem. 21B (1982), p. 371; J. Med. Chem. 24 (1981), p. 59), preferably by reaction with the sodium salt of 3-nitrobenzenesulfonic acid in an alkaline aqueous medium at a temperature of from 60° to 100° C.

The reaction proceeds as follows:

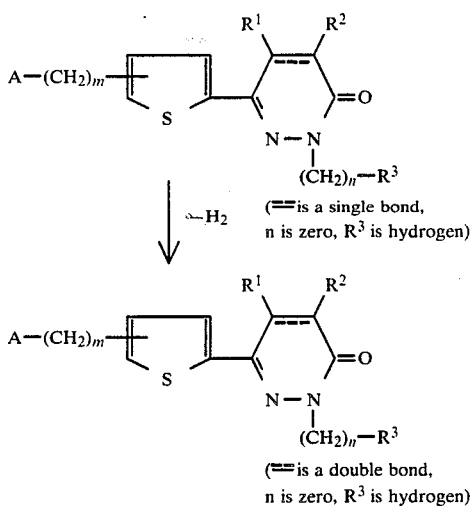

In addition to the above mentioned 6-(thien-2-yl)-3(2H)-pyridazinones of formula I wherein ≡≡≡≡ is a single bond, the following compounds may be used as starting compounds for dehydrogenation:

4,5-Dihydro-6-[5-(imidazol-1-yl-methyl)-thien-2-yl]-3(2H)-pyridazinone;

4,5-Dihydro-6-[5-(2-methyl-imidazol-1-yl-methyl)-thien-2-yl]-3(2H)-pyridazinone;

4,5-Dihydro-6-[4-(imidazol-1-yl-methyl)-thien-2-yl]-3(2H)-pyridazinone;

4,5-Dihydro-6-[4-(2-methyl-imidazol-1-yl-methyl)-thien-2-yl]-3(2H)-pyridazinone;

4,5-Dihydro-6-[5-[2-(imidazol-1-yl)ethyl]-thien-2-yl]-3(2H)-pyridazinone;

4,6-Dihydro-6-[5-[3-(imidazol-1-yl)-propyl]-thien-2-yl]-3(2H)-pyridazinone;

4,5-Dihydro-6-[5-[4-(imidazol-1-yl)-butyl]-thien-2-yl]-3(2H)-pyridazinone;

4,5-Dihydro-6-[5-[5-(imidazol-1-yl)-pentyl]-thien-2-yl]-3(2H)-pyridazinone;

4,5-Dihydro-6-[5-(imidazol-1-yl)-thien-2-yl]-3(2H)-pyridazinone;

4,5-Dihydro-6-[4-(imidazol-1-yl)-thien-2-yl]-3(2H)-pyridazinone;

4,5-Dihydro-6-[4-(imidazol-1-yl)-thien-2-yl]-5-methyl-3(2H)-pyridazinone;

4,5-Dihydro-6-[5-(imidazol-1-yl)-thien-2-yl]-5-methyl-3(2H)-pyridazinone;

4,5-Dihydro-6-[5-(2-methyl-imidazol-1-yl)-thien-2-yl]-5-methyl-3(2H)-pyridazinone;

4,5-Dihydro-6-[5-(imidazol-1-yl)-thien-2-yl]-4-methyl-3(2H)-pyridazinone;

4,5-Dihydro-6-[4-(imidazol-1-yl)-thien-2-yl]-4-methyl-3(2H)-pyridazinone.

The 3(2H)-pyridazinones of formuly I where ≡≡≡≡ is a double bond, n is not zero, and R³ is not H, can also be prepared from the corresponding 3(2H)-pyridazinones of formula I where n is zero, R³ is H and ≡≡≡≡ is a double bond, by reacting them in a suitable organic solvent, such as dimethylformamide, dimethylsulfoxide or hexamethylphosphoric acid-triamide, optionally in the presence of an auxiliary base such as sodium hydroxide or potassium carbonate, with an alkylating agent of formula III

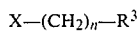   III wherein R³ is the same meaning as in formula I except hydrogen, n is an integer from 2 to 4 and X is a suitable split-off-group such as chlorine in a chloride, bromine in a bromide, iodine in an iodide, a methylsulfate or a tosylate group.

For example, the following compounds may be used as alkylating agents of formula III:

1-Chloro-2-diethylaminoethan, 1-chloro-3-diethylaminopropane,

1-Chloro-4-diethylaminobutane, 4-(2-chloroethyl)-morpholine, 4-(3-chloropropyl)-morpholine, 4-(4-chlorobutyl)-morpholine, 1(2-chloroethyl)-piperidine, 1-(3-chloropropyl)-piperidine, 1-(4-chlorobutyl)-piperidine, 1-(2-chloroethyl)-pyrrolidine, 1-(3-chloropropyl)-pyrrolidine, 1-(4-chlorobutyl)-pyrrolidine.

The acid addition salts of compounds of formula I with inorganic or organic acids can be prepared by mixing the starting compounds with the corresponding acids in aqueous, aqueous-organic (for example alcohol-water) or organic media, such as alcohols, alcohol-ether-mixtures or ether-petrolether-mixtures, at temperatures between 0° and 100° C.

The effectiveness of the compounds of the present invention is proved in pharmacological standard tests, as by the increase of the contractility of isolated ateria of guinea pigs, the increase of the contractility of the myocard in anesthesized cats at a simultaneously low change of blood pressure and heart pulse frequency of the test animal as well as the strong affinity of some compounds of the present invention to benzodiazepine receptors and imipramine fixation sites.

I. Test to show inotropic effectiveness in the isolated atrium of guinea pigs.

The measurements have been effected on isolated atria of guinea pigs. The effect to pulse frequency (chronotropy) is determined at the spontaneously pulsing right-hand atrium. The effect to the contractility (inotropy) is determined at the electrically stimulated left-hand atrium. The mean values of the percentage change to the starting value from six different determinations in each test is given hereinafter.

The test values for the following compounds are given:

A:  6-[5-(Imidazol-1-yl-methyl)-thien-2-yl]-3(2H)-pyridazinone (Example 4)

B:  3-Amino-5-(4-pyridyl)-2-pyridone (Amrinon)

| Test Compound | Concentration [mol/l] | Chronotropic Effect [%] | Inotropic Effect [%] |
|---|---|---|---|
| A+ | 1 × 10⁻⁴ | +19 | +44 |
| B++ | 1 × 10⁻⁴ | +2 | +4 |
|  | 1 × 10⁻³ | +20 | +21 |

+meassured in 1 × 10⁻⁴ molar citric acid solution
++meassured in tetraglycol and dilute hydrochlorid acid II. Determination of the myocardial effect in the narcotized cat.

10 cats of both sexes are narcotized with chloralose-urethane (0.25% urethane, 0.05% chloralose per kilogram). To ease the spontaneous respiration there was effected a tracheotomy. The following hemodynamic parameters were noted down:

The arteriel systolic and diastolic blood pressure by means of a polyethylene cathether in the right-hand Arteria femoralis registered by means of a Statham element type P23 DB. The pulse frequency was obtained from the blood pressure amplitude and registered by means of a cardiotachometer (type EKA-pulse).

The increase of isovolumetric blood pressure was determined by means of a catheter tip manometer of the type PC 350 A of the Millar Company, USA, introduced to the Arteria carotis communis left-ventricullary and was determined by subsequent differentiation (amplifier of Messrs. Sachs).

The known values have been registered continuously by a Beckmann-Dynograph of the type R. There are given the values in an interval of 2 minutes.

The test animals have been heparinized with 500 I.E. of Liquemin ®.

The test compounds are dissolved as follows:
Compound A in 50% glycofurol with heating,
Compound B in 10% glycofurol and 5% HCl with heating.

The test compounds have been administered at consecutively increasing dosages at a volume of 0.1 cc./kg. (Arteria femoralis). The total time of injection was 60 hours. The next dose has been administered only after the complete dying-out of the effect of the previous administration.

H—4-Methyl-2-(2-morpholino-ethyl)-6-phenyl-3(2H)-pyridazinon-hydrochloride
(Netherland Patent Application No. 6.602.599 which corresponds with U.S. Pat. No. 3,441,565; C.A. 66, 28791v (1976))

The determination of their inhibitory activity has been effected corresponding to H. W. Damm et al., Res. Comm. chem. path. Pharmacol. 22, 597–600 (1978) or, respectively, M. Briley et al., Eur. J. Pharmacol. 72, 377–380 (1981). The separation of the bound from the free ligand concentration is effected by filtration. The used ligands Flunitrazepam and Imipramin has been marked by tritium.

| | Half maximum inhibitory values have been determined by means of a log-probit-analysis | | | | | |
|---|---|---|---|---|---|---|
| | $^3$H—Flunitrazepam % Inhibition | | | $^3$H—Imipramin % Inhibition | | |
| Test Compound | $1 \times 10^{-6}$ mole/l | $1 \times 10^{-4}$ mole/l | IC$_{50}$ [mole/l] | $1 \times 10^{-6}$ mole/l | $1 \times 10^{-4}$ mole/l | IC$_{50}$ [mole/l] |
| D | 2 | 49 | $6 \times 10^{-5}$ | 34 | 87 | $2 \times 10^{-5}$ |
| E | 19 | 74 | $9 \times 10^{-6}$ | 4 | 40 | |
| F | 12 | 66 | $9 \times 10^{-5}$ | 7 | 62 | $7 \times 10^{-6}$ |
| G | 4 | 40 | | 27 | 86 | $3 \times 10^{-6}$ |
| H | 0 | 14 | | 8 | 36 | |
| Amitriptylinoxid | | | | | | $2.4 \times 10^{-5}$ |
| Medazepam | | | $3.9 \times 10^{-6}$ | | | |

Present invention also refers to pharmaceutical preparations for human therapy containing a compound of formula I or a pharmaceutically acceptable acid addition salt of these compounds. The pharmaceutical preparations of the invention are those for enteric, such as oral or rectal as well as parenteral administration which contain the pharmaceutically active compounds alone or together with a usual pharmaceutically usable carrier material. The pharmaceutical preparations of the active compound have the form of a single dose adapted to the desired application route, such as tablets, dragees, capsules, suppositories, granulates, solutions, emulsions or suspensions. The dosage of the compounds normally is between 1 and 500 mg per day, preferably between 10

| | Test Compound A | | | | Test Compound B | | | |
|---|---|---|---|---|---|---|---|---|
| | Myocardial | Pulse | Blood Pressure | | Myocardial | Pulse | Blood Pressure | |
| Dosage [mg/kg i.v.] | Contractility [%] | Frequency [%] | syst. [%] | diast. [%] | Contractility [%] | Frequency [%] | syst. [%] | diast. [%] |
| 0.1 | +24 | +1 | +1 | −1 | +5 | 0 | −3 | −3 |
| 0.316 | +32 | +1 | 0 | −6 | +25 | +1 | −2 | −4 |
| 1.0 | +42 | −9 | −8 | −18 | +40 | 0 | −15 | −22 |
| 3.16 | +51 | −15 | −19 | −33 | +30 | −20 | −35 | −51 |

III. Determination of activity to central nervous system.

The following compounds have been tested for their activity to benzodiazepin-receptors and imipramin-fixation sites in comparison to the known compounds Amitriptylinoxid and Medazepam:

D—2-(2-Morpholino-ethyl)-6-[5-(pyrazol-1-yl-methyl)-thien-2-yl]-3(2H)-pyridazinon-hydrochloride (Example 9)

E—6-[5-(Imidazol-1-yl-methyl)-thien-2-yl]-2-(2-morpholino-ethyl)-3(2H)-pyridazinon-hydrochloride F—6-[5-(Imidazol-1-yl-methyl)-thien-2-yl]-2-(2-piperidino-ethyl)-3(2H)-pyridazinon-hydrochloride G—6-[5-(Imidazol-1-yl-methyl)-thien-2-yl]-2-(3-piperidino-propyl)-3(2H)-pyridazinon-hydrochloride and 150 mg per day, and can be given once or several times, preferably two and three times daily.

The preparation of the compounds of the invention is further illustrated by the following examples. The melting points stated therein were determined by means of a Büchi 510 melting apparatus and are stated in °C. and not corrected. The IR spectra were taken by means of a Perkin Elmer 257 and a Nicolet NIC-3600, respectively, and the means spectra were taken by means of a Varian MAT-311A (70 eV).

EXAMPLE 1

4.5-Dihydro-6-[5-(pyrrolidin-1-yl-methyl)-thien-2-yl]-3(2H)-pyridazinone

A mixture of 9.2 g of succinic acid methylesterchloride in 20 ml of 1.2-dichloroethane are added with cooling with ice to a mixture of 18 g of aluminum chloride and 200 ml of dichloroethane. Thereafter, 10 g of 2-(pyrrolidin-1-yl-methyl)-thiophene (prepared by alkylating pyrrolidine with 2-chloromethyl-thiophene in toluene) are added dropwise. The mixture is stirred at 50° C. for 3 hours. Thereafter, the reaction mixture is added to a mixture of 50 g of ethylene diamino-tetraacetic acid and 500 ml of ice water. The pH of the reaction mixture is adjusted to 8.5 by the addition of dilute soda lye. The phases are separated, the organic phase is dried over sodium sulfate and is evaporated. The residual crude 4-[5-(pyrrolidin-1-yl-methyl)-thien-2-yl]-4-oxo-butyric acid methylester (14.4 g) is dissolved in 100 ml of methanol. After adding 2.5 g of sodium hydroxide, the mixture is stirred at 20° C. for 10 hours. It is evaporated thereafter, the residue is dissolved in water and the aqueous solution is shaken with chloroform. The aqueous phase is brought to a pH 6.7 by the addition of dilute hydrochloric acid. After adding 2 ml of hydrazine hydrate, the mixture is stirred at 100° C. for 2 hours. After cooling, the precipitated solid material is filtered off with suction, washed with water and dried.

Yield: 1.3 g.
Decomposition point: 125° to 126° C.
IR (in KBr): 1674 cm$^{-1}$.
MS [m/e]: 263 (M$^+$, 30%), 193 (100%), 151 (8%), 122 (18%).

EXAMPLE 2

4.5-Dihydro-6-[5-pyrrol-1-yl-methyl)-thien-2-yl]-3(2H)-pyridazinone.

(a) 4-[5-Pyrrol-1-yl-methyl)-thien-2-yl]-4-oxo-butyric acid.

63.2 g of succinic acid methylether chloride is added to a mixture of 123 g of aluminum chloride and 400 ml of 1.2-dichloroethane with cooling. Thereafter, 68.5 g of 2-(pyrrol-1-yl-methyl)-thiophene (prepared analogously to J. Med. Chem. 1981, 24, pgs. 59–63, from 2.5-dimethoxytetrahydrofurane and 2-aminomethyl-thiophene in acetic acid) are added dropwise. The reaction mixture is stirred at 50° C. for 3 hours. Thereafter, it is added to a mixture of 345 g of ethylene-diaminotetraacetic acid and 2 l of ice water and the pH is adjusted to 8.5 by the addition or dilute soda lye. After phase separation, the organic phase is dried over sodium sulfate and evaporated. The residual crude 4-[5-(pyrrol-1-yi-methyl)-thien-2-yl]-4-oxo-butyric acid methylester (64 g) is dissolved in 300 ml of methanol. After adding 9.2 g of sodium hydroxide, the mixture is stirred at 20° C. for 24 hours. Thereafter, the reaction mixture is evaporated, the residue is dissolved in water and extracted with ether. The aqueous phase is adjusted to pH 6.5 by the addition of dilute hydrochloric acid, the precipitate solid material is filtered off with suction, washed with water and dried.

Yield: 20 g.
Decomposition point: 117° to 120° C.
IR (in KBr): 1710, 1660 cm$^{-1}$.
MS [m/e]: 263 (M$^+$, 66%), 197 (100%), 190 (7%), 162 (5%), 151 (10%), 123 (10%), 97 (32%).

(b) 4.5-Dihydro-6-[5-(pyrrol-1-yl-methyl)-thien-2-yl]-3(2H)-pyridazinone.

A mixture of 18 g of 4-[5-(pyrrol-1-yl-methyl)-thien-2-yl]-4-oxo-butyric acid, 4.1 g of hydrazine hydrate and 200 ml of water is stirred for 2 hours at 95° C. After cooling, the precipitate solid material is filtered off with suction, washed with water and dried.

Yield: 10 g.
Decomposition point: 176° to 178° C.
IR (in KBr): 1674 cm$^{-1}$.
MS [m/e]: 259 (M$^+$, 24%), 193 (100%), 151 (8%), 122 (21%).

EXAMPLE 3

4.5-Dihydro-6-[5-(pyrazol-1-yl-methyl)-thien-2-yl]-3(2H)-pyridazinone.

(a) 4-[5-(pyrazol-1-yl-methyl)-thien-2-yl]-4-oxo-butyric acid-methylester.

62.4 g of succinic acid methylether chloride are added to a mixture of 180 g of aluminum and 800 ml of 1.2-dichloroethane with cooling. Thereafter, 78 g of 2-(pyrazol-1-yl-methyl)-thiophen (prepared by alkylating pyrazole with 2-chloromethylthiophen in dimethylformamid by usind sodium hydride, b.p. 82° C./0.35 torr) are added dropwise. Thereafter, the reaction mixture is stirred at 50° C. for 3 hours and then is added to a mixture of 503 g of ethylene-diamino-tetraacetic acid and 2.5 l of ice water. By the addition of dilute soda lye, the pH is adjusted to 8.5, the mixture is shaken, the organic phase is separated, dried over sodium sulfate and evaporated.

Yield: 75 g.
Melting point: 89° C.
IR (in KBr): 1726, 1660 cm$^{-1}$.
MS [m/e]: 278 (M$^+$, 52%), 247 (19%), 211 (11%), 191 (100%).

(b) 4-[5-(pyrazol-1-yl-methyl)-thien-2-yl]-4-oxo-butyric acid.

54 g of 4-[5-(pyrazol-1-yl-methyl)-thien-2-yl]-4-oxo-butyric acid-methylester are dissolved in 500 ml of methanol. After adding 11.4 g of sodium hydroxide, the mixture is stirred at 20° C. for 24 hours. The reaction mixture is evaporated, the residue is dissolved in water, washed with chloroform and the water phase is adjusted to pH 6.4 by the addition of dilute hydrochlorid acid. The precipitated solid material is filtered off with suction, washed with water and dried.

Yield: 36.8 g.
Decomposition point: 129° to 131° C.
IR (in KBr): 1740, 1668 cm$^{-1}$.
MS [m/e]: 264 (M$^+$, 13%), 220 (4%), 197 (19%), 191 (100%), 163 (5%), 124 (25%).

(c) 4.5-Dihydro-6-[5-(pyrazol-1-yl-methyl)-thien-2-yl]-3(2H)-pyridazinone.

Analoguous to Example 2(b), the reaction is carried out with 29 g of 4-[5-(pyrazol-1-yl-methyl)-thien-2-yl]-4-oxo-butyric acid and 6.6 g of hydrazin hydrate in 100 ml water.

Yield: 26.4 g.
Decomposition point: 143° C.
IR (in KBr): 1672 cm$^{-1}$.
MS [m/e]: 260 (M$^+$, 100%), 193 (93%), 122 (20%).

EXAMPLE 4

6-[5-(Imidazol-1-yl-methyl)-thien-2-yl]-3(2H)-pyridazinone.

20 g of 4.5-dihydro-6-[5-(imidazol-1-yl-methyl)-thien-2-yl]-3(2H)-pyridazinone (EP No. 71 059, Example 1) are stirred under reflux together with 19.5 g of the sodium salt of 3-nitrobenzenesulfonic acid and 13.5 g of sodium hydroxide in b 250 ml of water for 1 hour. Thereafter, while the solution is still hot, acetic acid are added until pH 6.9. The solid material precipitated after cooling is filtered of with suction, washed with water and dried.

Yield: 8.4 g.

Decomposition point: 231° to 232° C.
IR (in KBr): 1676, 1656 cm$^{-1}$.
MS [m/e]: 258 (M+, 5%), 191 (100%), 134 (25%), 121 (17%).

EXAMPLE 5

6-[4-(Imidazol-1-yl-methyl)-thien-2-yl]-3(2H)-pyridazinone.

Analoguous to Example 4, the reaction is carried out with 3 g of 4.5-dihydro-6-[4-(imidazol-1-yl-methyl)-thien-2-yl]-3(2H)-pyridazinone (prepared analoguous to Example 3, m.p. 178° to 179° C.), 2.9 g of the sodium salt of 3-nitrobenzenesulfonic acid and 2 g of sodium hydroxide in 40 ml of water. The reaction mixture is neutralized by the addition of 2.5 ml of acetic acid.

Yield: 40 g.
Decomposition point: 204° to 206° C.
IR (in KBr): 1678, 1649 cm$^{-1}$.
MS [m/e]: 258 (M+, 28%), 191 (100%), 134 (14%), 91 (10%).

EXAMPLE 6

6-[5-Pyrrol-1-yl-methyl)-thien-2-yl]-3(2H)-pyridazinone.

Analoguous to Example 4, the reaction is carried out with 3 g of 4.5-dihydro-6-[5-(pyrrol-1-yl-methyl)-thien-2-yl]-3(2H)-pyridazinone (Example 2), 2.4 g of the sodium salt of 3-nitrobenzenesulfonic acid and 2 g of sodium hydroxide in 40 ml of water. The reaction mixture is neutralized by the addition of 2.5 ml of acetic acid.

Yield: 0.5 g.
Decomposition point: beginning at 215° C.
IR (in KBr): 1673, 1653 cm$^{-1}$.
MS [m/e]: 257 (M+, 45%), 191 (100%), 134 (17%), 121 (9%), 91 (8%).

EXAMPLE 7

6-[5-(Pyrazol-1-yl-methyl)-thien-2-yl]-3(2H)-pyridazinone.

Analoguous to Example 4, the reaction is carried out with 20 g of 4.5-dihydro-6-[5-(pyrazol-1-yl-methyl)-thien-2-yl]-3(2H)-pyridazinone (Example 3), 19.2 g of the sodium salt of 3-nitrobenzenesulfonic acid and 13.5 g of sodium hydroxide in 200 ml of water. The reaction mixture is neutralized by the addition of 16 ml of acetic acid.

Yield: 5.9 g.
Decomposition point 185° to 188° C.
IR (in KBr): 1671, 1653 cm$^{-1}$.
MS [m/e]: 258 (M+, 73%), 225 (8%), 191 (100%), 134 (34%), 121 (25%), 91 (14%).

EXAMPLE 8

6-[5-(Imidazol-1-yl)-thien-2-yl]-5-methyl-3(2H)-pyridazinone.

(a) 4-[5-(Imidazol-1-yl)-thien-2-yl]-3-methyl-4-oxobutyric acid nitrile.

A mixture of 14.7 g of 5-(imidazol-1-yl)-thiophen-2-aldehyde (prepared analoguous to J. B. Polya et al., Chem. Soc. C. (1970), p. 85 ff., m.p. 105° to 107° C.), 5.5 g of 2-butenic acid nitrile, 0.81 g of sodium cyanide and 200 ml of dimethylformamide is stirred for 15 hours at 25° C. in a nitrogen atmosphere. After the addition of water, the reaction mixture is extracted with chloroform and the chloroform phase is washed with water, dried and evaporated. The residue is purified by column chromatography (silica gel//chloroform/methanol).

Yield: 9.4 g.
Melting point: 112° to 114° C.
IR (in KBr): 2245, 1648 cm$^{-1}$.
MS [m/e]: 245 (M+, 37%), 177 (100%), 149 (17%), 122 (8%), 105 (14%).

(b) 4-[5-(Imidazol-1-yl)-thien-2-yl]-3-methyl-4-oxobutyric acid.

6.7 g of 4-oxo-butyric acid nitrile are heated in 50 ml of 18% hydrochloric acid for 3 hours under reflux. After cooling, the pH is adjusted to 9 by the addition of sodium hydroxide and the reaction mixture is washed with chloroform. Thereafter, the pH is adjusted to 6.5.

The precipitated solid material is filtered off with suction and is dried. The filtrate is concentrated to a residual volume of 80 ml and used in the next step without further purification.

Yield: 0.45 g.
Melting point: 180° to 182° C.
IR (in KBr): 1721, 1638 cm$^{-1}$.
MS [m/e]: 264 (M+, 30%), 177 (100%), 149 (17%), 122 (8%), 105 (16%).

(c) 4.5-Dihydro-6-[5-(imidazol-1-yl)-thien-2-yl]-5-methyl-3(2H)-pyridazinone.

The aqueous solution of Example 8(b) is stirred with 3 ml of hydrazine hydrate for 2 hours at 90° C. The solid material precipitated upon cooling is recrystallized in a little amount of chloroform.

Yield: 3.3 g.
Melting point: 239° to 241° C.
IR (in KBr): 1677 cm$^{-1}$.
MS [m/e]: 260 (M+, 100%), 245 (12%), 203 (16%), 189 (14%), 175 (6%), 149 (6%).

(d) 6-[5-(Imidazol-1-yl)-thien-2-yl]-5-methyl-3(2H)-pyridazinone.

Analoguous to Example 4, the reaction is carried out with 2 g of the compound of Example 8(c), 1.9 g of the sodium salt of 3-nitrobenzenesulfonic acid and 1.35 g of sodium hydroxide in 30 ml of water. The reaction mixture is neutralized by the addition of 1.4 ml of acetic acid.

Yield: 1.1 g.
Decomposition point: 275° C.
IR (in KBr):1669 cm$^{-1}$.
MS [m/e]: 258 (M+, 100%), 225 (7%), 201 (69%), 134 (11%).

6-[4-(Imidazol-1-yl)-thien-2-yl]-5-methyl-3(2H)-pyridazinone.

4-Bromo-thiophen-2-aldehyde is reacted with imidazol to 4-(imidazol-1-yl)-thiophen-2-aldehyde which is reacted with the necessary acid nitrile to 4-[4-(imidazol-1-yl)-thien-2-yl]-4-oxo-butyric acid nitrile which is hydrolized to 4-[4-(imidazol-1-yl)-thien-2-yl]-4-oxobutyric acid. This compound is reacted with hydrazine hydrate to yield 4.5-dihydro-6-[4-(imidazol-1-yl)-thien-2-yl]-3-(2H)-pyridazinone which is subsequently dehydrogenated with 3-nitrobenzolsulfonic acid.

Fp.: 296° to 298° C.
IR (in KBr): 1671, 1650 cm$^{-1}$.
MS [m/e]: 244 (M+, 100%), 217 (4%), 187 (23%), 160 (6%), 120 (6%).

6-[4-(Imidazol-1-yl)-thien-2-yl]-5-methyl-3(2H)-pyridazinone.

This product is prepared from 4-(imidazol-1-yl)-thiophen-2-aldehyde which is reacted with 2-butenic acid nitrile to yield 4-[4-(imidazol-1-yl)-thien-2-yl]-3-methyl-4-oxo-butyric acid nitrile. This compound is hydrolized to yield 4-[4-(imidazol-1-yl)-thien-2-yl]-3-methyl-4-oxobutyric acid which is subjected to reaction with hydrazine hydrate to yield 4.5-dihydro-6-[4-(imidazol-1-yl)- thien-2-yl]-5-methyl-3(2H)-pyridazinone which is dehydrogenated with 3-nitrobenzene sulfonic acid.

Fp.: 260° C.

IR (in KBr): 1667 cm$^{-1}$.

MS [m/e]: 258 (M+, 100%), 201 (26%), 134 (5%).

6-[4-Imidazol-1-yl)-thien-2-yl]-4-methyl-3(2H)-pyridazinone.

This product is produced from 4-(imidazol-1-yl)-thiophen-2-aldehyde which is reacted with methacrylo nitrile to yield 4-[4-(imidazol-1-yl)-thien-2-yl]-2-methyl-4-oxo-butyric acid nitrile. This compound is hydrolized to 4-[4-(imidazol-1-yl)-thien-2-yl]-2-methyl-4-oxo-butyric acid and which is subjected to reaction with hydrazine hydrate to yield 4.5-dihydro-6-[4-(imidazol-1-yl)-thien-2-yl]-4-methyl-3(2H)-pyridazinone.

This product is subsequently dehydrogenated with 3-nitrobenzene sulfonic acid.

Fp.: 250° C.

IR (in KBr): 1651 cm$^{-1}$.

MS [m/e]: 258 (M+, 100%), 213 (5%), 201 (20%), 174 (5%), 134 (4%), 129 (6%).

EXAMPLE 9

2-(2-Morpholino-ethyl)-6-[5-pyrazol-1-yl-methyl)-thien-2-yl]-3(2H)-pyridazinone hydrochloride.

A solution of 2.6 g of 6-[5-(pyrazol-1-yl-methyl)-thien-2-yl]-3(2H)-pyridazinone (Example 7) in 40 ml of dimethylformamide is added dropwise within 30 minutes to a suspension of 0.32 g of sodium hydride (80% mineral oil suspension) in 10 ml of dimethylformamide. After further stirring for 30 minutes at 30° C., a mixture of 1.4 g of N-(2-chloro-ethyl)-morpholine in 20 ml of dimethylformamide is added dropwise within 20 minutes. Thereafter, the mixture is stirred for 2 hours at 100° C. After cooling and evaporation, the residue is redissolved in 200 ml of water and the solution is extracted several times with chloroform. The chloroform phase is dried over sodium sulfate and is evaporated. The residue is dissolved in ethanolic hydrochloric acid and the hydrochloride is precipitated by the addition of ether, filtered off with suction and dried.

Yield: 3 g.

Decomposition point: 171° C.

IR (in KBr): 3420, 1662 cm$^{-1}$.

MS [m/e]: 371 (M+, 0.3%), 284 (1.8%), 258 (0.9%), 191 (3.4%), 113 (90.6%), 100 (100%).

Similar to Example 9 there are produced:

6-[5-(Imidazol-1-yl-methyl)-thien-2-yl]-2-(2-morpholinoethyl)-3(2H)-pyridazinone-hydrochloride.

This product is prepared from 6-[5-imidazol-1-yl-methyl)-thien-2-yl]-3(2H)-pyridazinone (Example 4) with N-(2-chloroethyl)-morpholine.

Decomposition point: 140° C.

IR (in KBr): 1661 cm$^{-1}$.

MS [m/e]: 371 (M+ —HCl, 1%), 259 (20%), 113 (38%), 100 (100%).

6-[6-(Imidazol-1-yl-methyl)-thien-2-yl]-2-(2-piperidinoethyl)-3(2H)-pyridazinone-hydrochloride.

This compound is prepared from 6-[5-(imidazol-1-yl-methyl)-thien-2-yl]-3(2H)-pyridazinone (Example 4) by subjecting it to reaction with N-(2-chloroethyl)-piperidine.

Decomposition point: 145° C.

IR (in KBr): 1662 cm$^{-1}$.

MS [m/e]: 301 (M+ —HCl-imidazol, 3%), 111 (31%) 98 (100%).

6-[5-Imidazol-1-yl)-methyl)-thien-2-yl]-2-(3-piperidinopropyl)-3(2H)-pyridazinone hydrochloride.

This product is prepared from 6-[5-(imidazol-1-yl-methyl)-thien-2-yl]-3(2H)-pyridazinone (Example 4) by subjecting it to reaction with N-(3-chloropropyl)-piperidine.

Decomposition point: 250° C.

IR (in KBr): 1656 cm$^{-1}$.

MS [m/e]: 383 (M+ —HCl, 0,1%), 315 (M+ —HCl-imidazol, 76%), 232 (19%), 124 (77%), 98 (100%).

6-[5-(Imidazol-1-yl-methyl)-thien-2-yl]-2-(pyrrolidinoethyl)-3(2H)-pyridazinone-hyrochloride.

This product is prepared from 6-[5-(imidazol-1-yl-methyl)-thien-2-yl]-3(2H)-pyridazinone (Example 4) by subjecting it to reaction with N-(2-chloroethyl)-pyrrolidine.

Decomposition point: 140° C.

IR (in KBr): 1662 cm$^{-1}$.

MS [m/e]: 355 (M+ —HCl, 0,1%), 287 (M+ —HCl-imidazol, 5%), 259 (3%), 191 (3%), 97 (54%), 84 (100%).

2-(2-Diethylamino-ethyl)-6-[5-(imidazol-1-yl-methyl)-thien-2-yl]-3(2H)-pyridazinone-hydrochloride.

This product is prepared from 6-[5-(imidazol-1-yl-methyl)-thien-2-yl]-3(2H)-pyridazinone (Example 4) by subjecting it to reaction with N-(2-choroethyl)-diethylamine.

Decomposition point: 100° C.

IR (in KBr): 1663 cm$^{-1}$.

MS [m/e]: 357 (M+ —HCl, 0,3%), 176 (2%), 99 (26%), 86 (100%).

6-[4-(Imidazol-1-yl)-thien-2-yl]-4-methyl-2-(2-morpholino-ethyl)-3(2H)-pyridazinone-hydrochloride.

This product is prepared from 6-[4-(imidazol-1-yl)-thien-2-yl]-4-methyl-3(2H)-pyridazinone (Example 4) by subjecting it to reaction with N-(2-chloroethyl)-morpholine.

Decomposition point: 300° C.

MS [m/e]: 371 (M+ —HCl, 0.5%), 259 (8%), 113 (56%), 100 (100%).

What we claim is:

1. The substituted 6-(thien-2-yl)-3(2H)-pyridazinones of formula I

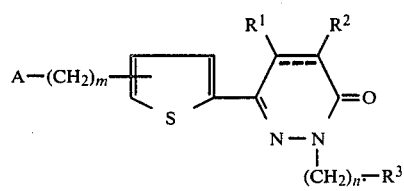

wherein

A is a member selected from the group consisting of the saturated, the partly saturated and the heteroaromatic five-membered heterocycles containing as the sole heteroatoms 1 to 3 nitrogen atoms, the heterocyclic group being bonded to the neighbouring carbon atom through one of its nitrogen atoms and being unsubstituted or substituted by 1 or 2 $C_{1-4}$-lower alkyl radicals, m is zero or an integer from 1 to 5, $R^1$ and $R^2$ which may be the same of different from each other, are members selected from the group consisting of hydrogen and methyl, n is zero or an integer from 2 to 4, $R^3$ is a member selected from the group consisting of hydrogen, if n is zero, and the di-$C_{1-4}$ lower alkylamino groups, the morpholino, the pyrrolidino and the piperidino group, if n is not zero, and
━━━ is a double bond, and the pharmacologically acceptable acid addition salts thereof with inorganic and organic acids.

2. The 6-(thien-2-yl)-3(2H)-pyridazinones according to claim 1 wherein in Formula I A is a member selected from the group consisting of the saturated, the partly saturated and the heteroaromatic five-membered heterocycles containing 1 to 3 nitrogen atoms bonded to the neighbouring carbon atom through one of its nitrogen atoms and being unsubstituted or substituted by a methyl group, m is zero or an integer from 1 to 5, $R^1$ and $R^2$ which may be the same or different from each other, are members selected from the group consisting of hydrogen and methyl, n is zero or an integer from 2 to 4, $R^3$ is a member selected from the group consisting of hydrogen, if n is zero, and the di-$C_{1-4}$-lower alkylamino groups, the morpholino, pyrrolidino and piperidino group, if n is not zero, and
━━━ is a double bond, and the pharmacologically acceptable salts thereof with inorganic and organic acids, the above named compounds being in equilibrium with the tautomeric 3-hydroxy-pyridazines, if n is zero and $R^3$ is hydrogen.

* * * * *